US011166902B2

(12) United States Patent
Teboul

(10) Patent No.: US 11,166,902 B2
(45) Date of Patent: Nov. 9, 2021

(54) COMPOSITION COMPRISING A COMBINATION OF AN ACRYLIC POLYMER, A SILICONE COPOLYMER AND AN AMINO ACID OR AMINO ACID DERIVATIVE

(71) Applicant: L'OREAL, Paris (FR)

(72) Inventor: Karen Teboul, St Mande (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/899,718

(22) PCT Filed: Jun. 18, 2014

(86) PCT No.: PCT/EP2014/062807
§ 371 (c)(1),
(2) Date: Dec. 18, 2015

(87) PCT Pub. No.: WO2014/202655
PCT Pub. Date: Dec. 24, 2014

(65) Prior Publication Data
US 2016/0143841 A1 May 26, 2016

(30) Foreign Application Priority Data
Jun. 20, 2013 (FR) ....................... 1355826

(51) Int. Cl.
*A61K 8/04* (2006.01)
*A61K 8/44* (2006.01)
*A61K 8/81* (2006.01)
*A61K 8/895* (2006.01)
*A61Q 5/06* (2006.01)
*A61Q 5/00* (2006.01)
*A61K 8/64* (2006.01)

(52) U.S. Cl.
CPC .............. *A61K 8/895* (2013.01); *A61K 8/04* (2013.01); *A61K 8/44* (2013.01); *A61K 8/64* (2013.01); *A61K 8/645* (2013.01); *A61K 8/8141* (2013.01); *A61K 8/8152* (2013.01); *A61Q 5/002* (2013.01); *A61Q 5/06* (2013.01); *A61Q 5/065* (2013.01); *A61K 2800/43* (2013.01); *A61K 2800/436* (2013.01); *A61K 2800/594* (2013.01)

(58) Field of Classification Search
CPC . A61K 8/895; A61K 8/04; A61K 8/44; A61K 8/64; A61K 8/645; A61K 8/8141; A61K 8/8152; A61Q 5/002; A61Q 5/06; A61Q 5/065

See application file for complete search history.

(56) References Cited

U.S. PATENT DOCUMENTS

| | | | |
|---|---|---|---|
| 4,185,087 A | 1/1980 | Morlino | |
| 4,578,266 A | 3/1986 | Tietjen et al. | |
| 5,601,808 A * | 2/1997 | Mellul | A61K 8/8152 424/401 |
| 5,645,609 A | 7/1997 | Andrean et al. | |
| 5,961,665 A | 10/1999 | Fishman | |
| 5,990,479 A | 11/1999 | Weiss et al. | |
| 6,013,250 A | 1/2000 | Cannell et al. | |
| 6,024,946 A | 2/2000 | Dufief et al. | |
| 6,123,930 A * | 9/2000 | Agnus et al. | |
| 6,225,198 B1 | 5/2001 | Alivisatos et al. | |
| 7,942,937 B2 | 5/2011 | Brun | |
| 8,936,779 B2 | 1/2015 | Pasquet et al. | |
| 9,517,188 B2 * | 12/2016 | Crane | |
| 2002/0085986 A1 * | 7/2002 | De La Poterie | |
| 2003/0171479 A1 * | 9/2003 | Lennon | A61K 8/06 524/501 |
| 2003/0175229 A1 | 9/2003 | Giroud | |
| 2004/0131577 A1 | 7/2004 | Davies et al. | |
| 2005/0191264 A1 * | 9/2005 | Detert | |
| 2005/0220728 A1 * | 10/2005 | Kanji | |
| 2007/0190016 A1 | 8/2007 | Pasquet et al. | |
| 2007/0298003 A1 * | 12/2007 | Chandra | A61K 8/60 424/70.12 |
| 2009/0151086 A1 | 6/2009 | Brun | |
| 2009/0214458 A1 | 8/2009 | Brun et al. | |
| 2009/0324658 A1 * | 12/2009 | Nohata | |
| 2010/0083446 A1 | 4/2010 | Brun et al. | |
| 2011/0044933 A1 * | 2/2011 | Dorr | A61K 8/42 424/78.37 |
| 2011/0300092 A1 * | 12/2011 | Kambach | |
| 2013/0084256 A1 | 4/2013 | Li et al. | |

(Continued)

FOREIGN PATENT DOCUMENTS

| | | |
|---|---|---|
| CN | 1254276 A | 5/2000 |
| CN | 101015511 A | 11/2012 |
| CN | 101455622 A | 2/2013 |

(Continued)

OTHER PUBLICATIONS

Tood, Charles, et al., "Volatile Silicone Fluids for Cosmetic Formulations," Cosmetics and Toiletries, vol. 91, Jan. 1976, pp. 29-32.
Dabbousi, B.O., et al., "(CdSe)ZnS Core-Shell Quantum Dots: Synthesis and Characterization of a Size Series of Highly Luminescent Nanocrystallites," Journal of Physical Chemistry B, vol. 101, 1997, pp. 9463-9475.
Peng, Xiaogang et al., "Epitaxial Growth of Highly Luminescent CdSe/CdS Core/Shell Nanocrystals with Photostability and Electronic Accessibility," Journal of the American Chemical Society, vol. 119, No. 30, 1997, pp. 7019-7029.
"Perfumes," Kirk-Othmer Encyclopedia of Chemical Technology, Fourth Edition, vol. 18, 1996, pp. 171-200.
English machine translation of JP05-017710A (Jan. 26, 1993).
English language Abstract of JP07-258460A (Oct. 9, 1995).
English machine translation of JP09-188830A (Jul. 22, 1997).

(Continued)

*Primary Examiner* — Alma Pipic
(74) *Attorney, Agent, or Firm* — The Marbury Law Group, PLLC

(57) ABSTRACT

The present invention relates to a composition for treating keratin fibres, comprising at least an aqueous dispersion of hybrid hydrophobic film-forming acrylic polymer particles, at least one linear block silicone copolymer and at least one amino acid or amino acid derivative.

11 Claims, No Drawings

(56) References Cited

U.S. PATENT DOCUMENTS

2014/0246038 A1 9/2014 Teboul et al.

FOREIGN PATENT DOCUMENTS

| | | | |
|---|---|---|---|
| EP | 0095238 | A2 | 11/1983 |
| EP | 0530974 | A1 | 3/1993 |
| EP | 0874017 | A2 | 10/1998 |
| EP | 1184426 | A2 | 3/2002 |
| EP | 1591102 | A1 | 11/2005 |
| EP | 1800658 | A1 | 6/2007 |
| EP | 2070516 | A1 | 6/2009 |
| EP | 2095810 | A1 | 9/2009 |
| FR | 2679771 | A1 | 2/1993 |
| FR | 2833489 | A1 | 6/2003 |
| FR | 2936414 | A1 | 4/2010 |
| FR | 2976461 | A1 | 12/2012 |
| JP | 05-017710 | A | 1/1993 |
| JP | 07-258460 | A | 10/1995 |
| JP | 09-188830 | A | 7/1997 |
| JP | 10-158450 | A | 6/1998 |
| JP | 10-158451 | A | 6/1998 |
| WO | 92/21316 | A1 | 12/1992 |
| WO | 98/51265 | A1 | 11/1998 |
| WO | 2010/149493 | A2 | 12/2010 |
| WO | 2014/202658 | A1 | 12/2014 |

OTHER PUBLICATIONS

English machine translation of JP10-158450A (Jun. 16, 1998).
English machine translation of JP10-158451A (Jun. 16, 1998).
International Search Report for PCT/EP2014/062807, dated Jul. 28, 2014.
International Search Report for PCT/EP2014/062812, dated Jul. 28, 2014.
Non-Final Office Action for co-pending U.S. Appl. No. 14/899,724, dated Sep. 13, 2016.
Office Action for counterpart Application CN 201480034910.X dated Dec. 11, 2017.
Office Action for counterpart Application CN 201480034910.X dated Feb. 28, 2017.
Office Action for counterpart Application CN201480035002.2, dated Apr. 1, 2017.
Annex to Communication for counterpart Application No. EP14733121 dated Mar. 27, 2017.
Communication for counterpart Application No. EP14733121 dated Mar. 27, 2017.
http://www.gnpd.com—Mintel Uptight Heat Activated Curl Maker, dated Oct. 2001.
Office Action for Counterpart Application No. CN201480034910.X, dated Dec. 11, 2017.
Final Office Action for copending U.S. Appl. No. 14/899,724, dated Apr. 20, 2017.
Final Office Action for copending U.S. Appl. No. 14/899,724, dated Oct. 3, 2017.
Notice of Allowance for copending U.S. Appl. No. 14/899,724, dated Aug. 24, 2018.

* cited by examiner

COMPOSITION COMPRISING A COMBINATION OF AN ACRYLIC POLYMER, A SILICONE COPOLYMER AND AN AMINO ACID OR AMINO ACID DERIVATIVE

CROSS REFERENCE TO RELATED APPLICATIONS

This is a national stage application of PCT/EP2014/062,807, filed internationally on Jun. 18, 2014, which claims priority to French Application No. 1355826, filed on Jun. 20, 2013, both of which are herein incorporated by reference in their entireties.

The present invention relates to a composition for treating keratin fibres, comprising an aqueous dispersion of particles of a particular acrylic polymer, a linear block silicone copolymer and an amino acid or an amino acid derivative, and also to a process for treating keratin fibres using such a composition.

The hair is generally damaged and embrittled by the action of external atmospheric agents such as light and bad weather, and by mechanical or chemical treatments, such as brushing, combing, bleaching, permanent-waving and/or dyeing. As a result, the hair is often difficult to manage and in particular is difficult to disentangle or style, and a head of hair, even of lush hair, has difficulty in maintaining an attractive style due to the fact that the hair lacks vigour, volume and liveliness.

This degradation to the hair is increased, moreover, by the repetition of permanent hair colouring treatments, which involves applying to the hair one or more dye precursors and an oxidizing agent.

Thus, to overcome this, it is now common practice to use styling products that allow the hair to be conditioned by especially giving it body, mass or volume.

These styling products are generally cosmetic hair compositions comprising one or more polymers with high affinity for the hair, which often have the function of forming a film on the hair surface in order to modify its surface properties and especially to condition it or to give it particular optical properties.

One drawback associated with the use of these hair compositions lies in the fact that the cosmetic effects imparted by such compositions have a tendency to disappear, especially at the first shampoo wash.

In order to overcome this drawback, it may be envisaged to increase the persistence of the deposit of polymers by directly performing free-radical polymerization of certain monomers on the hair. However, the treatments thus obtained result in the degradation of the fibre and the hair thus treated is generally difficult to disentangle.

It is moreover known practice to coat the hair with a composition comprising an electrophilic monomer of cyanoacrylate type, especially in patent application FR 2 833 489. Such a composition makes it possible to obtain perfectly coated and non-greasy hair. However, the coating obtained necessitates specific operating conditions, owing to the reactivity of the electrophilic monomer. Moreover, the coating obtained with these electrophilic monomers becomes tacky with fatty substances such as sebum.

It is also known practice, especially from document EP 2 095 810, to improve the persistence of the deposit on keratin fibres by applying a composition comprising a pressure-sensitive adhesive silicone copolymer, more commonly known as a BioPSA. The feel obtained with these copolymers is generally tacky. Hair treated with this type of composition has a slightly coarse and not entirely natural feel. Furthermore, the application of this type of composition is time-consuming and requires a step of total drying at a temperature above room temperature, for example with a hairdryer, which is obligatory in order to obtain long-lasting coating.

Document WO 92/21316 describes compositions based on silicone and latex. However, the results obtained with the compositions of the said document are unsatisfactory in terms of the coating effect and the persistence of the properties, especially with respect to shampooing.

Moreover, hair treatment products (gels, shampoos or products for caring for or conditioning the hair) are generally perfumed, but have very limited remanence of the perfume on the hair, the perfume generally fading after a few minutes or, in the best of cases, after a few hours.

Thus, the aim of the present invention is to develop a composition for treating keratin fibres, and in particular human keratin fibres such as the hair, which makes it possible to obtain coatings that are persistent with respect to shampooing and to the various attacking factors to which the hair may be subjected, especially blow-drying and perspiration, while at the same time showing better tolerance towards fatty substances such as sebum and not developing any tacky nature, this coating moreover being smooth and uniform on keratin fibres, leaving them perfectly individualized.

This aim is achieved with the present invention, one subject of which is thus a composition for treating keratin fibres, comprising at least an aqueous dispersion of particles of at least one hybrid hydrophobic film-forming acrylic polymer, at least one linear block silicone copolymer and at least one amino acid or amino acid derivative.

A subject of the invention is also a process for treating keratin fibres, comprising the application to the fibre(s) of the composition of the invention, the application optionally being followed by drying of the fibres.

The term "at least one" means "one or more".

The treatment composition of the invention makes it possible to obtain a coating that is persistent with respect to shampooing, while at the same time preserving the physical qualities of the keratin fibre. Such a coating is, in particular, resistant to the external attacking factors to which the fibres may be subjected, such as blow-drying and perspiration. It makes it possible in particular to obtain a smooth, uniform deposit. With the composition and the process of the invention, a persistent coating is obtained without it being necessary to dry the hair with a hairdryer. The hair after application is left in the open air, and after a few seconds the persistent coating is formed. The hairs are individualized. The term "individualized fibres" means fibres which, after application of the composition and drying, are not stuck together (or are all separate from each other) and therefore do not form clumps, since the coating is formed around virtually every fibre.

Aqueous Dispersion of Hybrid Acrylic Hydrophobic Film-Forming Polymer Particles

For the purposes of the invention, the term "polymer" means a compound corresponding to the repetition of one or more units (these units being derived from compounds known as monomers). This or these unit(s) are repeated at least twice and preferably at least three times.

The term "film-forming" polymer means a polymer that is capable, by itself or in the presence of an auxiliary film-forming agent, of forming a macroscopically continuous film on a support, especially on keratin materials, and preferably a cohesive film.

The term "hydrophobic polymer" means a polymer that has a solubility in water at 25° C. of less than 1% by weight.

The dispersion may be a simple dispersion in the aqueous medium of the composition. A particular case of dispersions that may be mentioned is lattices.

For the purposes of the present invention, the term "hybrid acrylic polymer" means a polymer synthesized from at least one compound (i) chosen from monomers bearing at least one (meth)acrylic acid group and/or esters of these acid monomers and/or amides of these acid monomers and from at least one compound (ii) different from the compounds (i), i.e. which does not comprise any (meth)acrylic acid groups and/or esters of these acid monomers and/or amides of these acid monomers.

The (meth)acrylic acid esters (also known as (meth) acrylates) are advantageously chosen from alkyl (meth) acrylates, in particular $C_1$-$C_{30}$, preferably $C_1$-$C_{20}$ and better still $C_1$-$C_{10}$ alkyl (meth)acrylates, aryl (meth)acrylates, in particular $C_6$-$C_{10}$ aryl (meth)acrylates, and hydroxyalkyl (meth)acrylates, in particular $C_2$-$C_6$ hydroxyalkyl (meth) acrylates.

Alkyl (meth)acrylates that may be mentioned include methyl methacrylate, ethyl methacrylate, butyl methacrylate, isobutyl methacrylate, 2-ethylhexyl methacrylate, lauryl methacrylate and cyclohexyl methacrylate.

Hydroxyalkyl (meth)acrylates that may be mentioned include hydroxyethyl acrylate, 2-hydroxypropyl acrylate, hydroxyethyl methacrylate and 2-hydroxypropyl methacrylate.

Aryl (meth)acrylates that may be mentioned include benzyl acrylate and phenyl acrylate.

The (meth)acrylic acid esters that are particularly preferred are the alkyl (meth)acrylates.

According to the present invention, the alkyl group of the esters may be either fluorinated or perfluorinated, i.e. some or all of the hydrogen atoms of the alkyl group are substituted with fluorine atoms.

Examples of amides of the acid monomers that may be mentioned are (meth)acrylamides, and in particular N-alkyl (meth)acrylamides, in particular of a $C_2$-$C_{12}$ alkyl. The N-alkyl(meth)acrylamides that may be mentioned include N-ethylacrylamide, N-t-butylacrylamide, N-t-octylacrylamide and N-undecylacrylamide.

As compounds (ii) different from the compounds (i), mention will be made, for example, of styrene monomers.

In particular, the acrylic polymer may be a styrene/acrylate copolymer, and especially a polymer chosen from copolymers derived from the polymerization of at least one styrene monomer and at least one $C_1$-$C_{20}$ and preferably $C_1$-$C_{10}$ alkyl acrylate monomer.

As styrene monomers that may be used in the invention, mention may be made of styrene and α-methylstyrene, and preferably styrene.

The $C_1$-$C_{10}$ alkyl acrylate monomer may be chosen from methyl acrylate, ethyl acrylate, propyl acrylate, butyl acrylate, hexyl acrylate, octyl acrylate and 2-ethylhexyl acrylate.

As acrylic polymers synthesized with styrene monomers, mention may be made of the styrene/acrylate copolymers sold under the name Joncryl 77 by the company BASF, under the name Yodosol GH41F by the company Akzo Nobel and under the name Syntran 5760 CG by the company Interpolymer.

As compound (ii), mention may also be made of compounds that interact via a process other than the radical polymerization of unsaturated compounds or the compounds derived from such a process. Such a process may be, for example, a polycondensation. As polycondensations, mention may be made of the formation of polyurethanes, polyesters or polyamides. Besides the acrylic monomer(s), the hybrid hydrophobic film-forming polymer of the invention will then contain the compound derived from the condensation process or the compounds that interact in the polycondensation process.

As film-forming hybrid acrylic copolymers of this type, mention may be made especially of the product sold under the reference Hybridur 875 Polymer Dispersion by the company Air Products & Chemicals.

As hybrid film-forming hydrophobic acrylic copolymer, use may also be made of the product sold under the reference Primal HG 1000 by the company Dow.

According to a particular embodiment, the hybrid film-forming acrylic polymer is a copolymer based on at least one styrene monomer and on at least one (meth)acrylic acid ester.

The hybrid hydrophobic film-forming acrylic polymer(s) in aqueous dispersion may be present in a content, as polymer active materials, ranging from 0.1% to 30% by weight, better still from 0.5% to 20% by weight and even better still from 1% to 15% by weight, relative to the total weight of the composition.

Linear Block Silicone Copolymer

The silicone copolymer used in the composition according to the invention is a linear block copolymer, i.e. a non-crosslinked copolymer, obtained by chain extension and not by crosslinking.

The term "block copolymer" (or "sequential copolymer") denotes a polymer comprising at least two different blocks (sequences). Each block of the polymer is derived from one type of monomer or from several different types of monomer. This means that each block may consist of a homopolymer or a copolymer; this copolymer constituting the block may in turn be random or alternating.

The silicone copolymer used in the composition according to the invention preferably comprises at least two different silicone blocks (or sequences), each block resulting from the polymerization of at least one type of silicone monomer or several types of silicone monomers, as described below.

It should also be noted that the copolymer is "linear", in other words the structure of the polymer is not branched, or in star form, or grafted.

The linear block silicone copolymer is advantageously in the form of particles in dispersion in an aqueous medium.

The aqueous dispersion of block copolymer particles is a silicone-in-water (Sil/W) emulsion, the oil globules of which consist of a silicone of high viscosity, such that these globules appear to form like "flexible particles".

The size of the linear block silicone copolymer particles may vary widely. Preferably, in the present patent application, the linear block silicone copolymer particles generally have a number-average size of less than or equal to 2 microns and preferably less than or equal to 1 micron.

The aqueous dispersions of linear block silicone copolymer particles used in the composition according to the invention may be chosen especially from those described in document EP-A-874 017, the teaching of which is incorporated herein by reference. According to the said document, the silicone copolymers constituting these particles may especially be obtained by a chain-extension reaction, in the presence of a catalyst, using at least:

(a) a polysiloxane (i) bearing at least one reactive group and preferably one or two reactive groups per molecule; and (b) an organosilicon compound (ii) which reacts with the polysiloxane (i) via a chain-extension reaction.

In particular, the polysiloxane (i) is chosen from the compounds of formula (I):

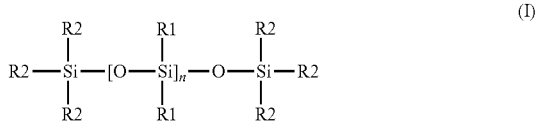

(I)

in which $R_1$ and $R_2$ represent, independently of each other, a hydrocarbon-based group containing from 1 to 20 carbon atoms and preferably from 1 to 10 carbon atoms, such as methyl, ethyl, propyl or butyl, or an aryl group, such as phenyl, or a reactive group, and n is an integer greater than 1, provided that there are on average between one and two reactive groups per polymer.

The term "reactive group" means any group that is capable of reacting with the organosilicon compound (ii) to form a block copolymer. Mention may be made, as reactive groups, of hydrogen; aliphatically unsaturated groups, in particular vinyl, allyl or hexenyl groups; the hydroxyl group; alkoxy groups, such as methoxy, ethoxy or propoxy groups; alkoxyalkoxy groups; the acetoxy group; amine groups, and mixtures thereof. Preferably, more than 90% and better still more than 98% of the reactive groups are at the end of a chain, i.e. the radicals $R_2$ generally constitute more than 90% and even 98% of the reactive groups.

n may especially denote an integer ranging from 5 to 30, preferably from 10 to 30 and better still from 15 to 25.

The polysiloxanes of formula (I) are linear polymers, that is to say comprising little branching and generally less than 2 mol % of siloxane units. Moreover, the groups $R_1$ and $R_2$ may be optionally substituted with amine groups, epoxy groups or groups comprising sulfur, silicon or oxygen.

Preferably, at least 80% of the groups $R_1$ are alkyl groups and better still methyl groups.

Preferably, the reactive group $R_2$ at the end of a chain is an aliphatically unsaturated group and especially vinyl.

A polysiloxane (i) that may especially be mentioned is dimethylvinylsiloxypolydimethylsiloxane, compound of formula (I) in which the radicals $R_1$ are methyl radicals and the radicals $R_2$ at the end of a chain are vinyl radicals, whereas the other two radicals $R_2$ are methyl radicals.

The organosilicon compound (ii) may be chosen from the polysiloxanes of formula (I) or compounds acting as chain extenders. If it is a compound of formula (I), the polysiloxane (i) will comprise a first reactive group and the organosilicon compound (ii) will comprise a second reactive group which will react with the first group. If it is a chain extender, it may be a silane, a siloxane (disiloxane or trisiloxane) or a silazane. Preferably, the organosilicon compound (ii) is a liquid organohydrogenpolysiloxane of formula (II):

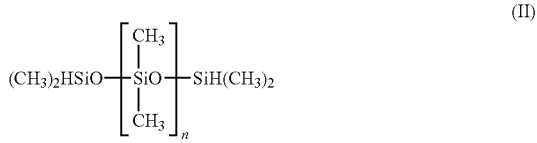

(II)

in which n is an integer greater than 1 and preferably greater than 10, for example ranging from 2 to 100, preferably from 10 to 30 and better still from 15 to 25. According to one particular embodiment of the invention, n is equal to 20.

The silicone block copolymers used according to the invention are advantageously free of oxyalkylene groups, especially free of oxyethylene and/or oxypropylene groups.

The catalyst for the reaction between the polysiloxane and the organosilicon compound may be chosen from metals and especially from platinum, rhodium, tin, titanium, copper and lead. It is preferably platinum or rhodium.

The silicone copolymer particle dispersion used in the composition according to the invention may especially be obtained, for example, by mixing (a) water, (b) at least one emulsifier, (c) the polysiloxane (i), (d) the organosilicon compound (ii) and (e) a catalyst. Preferably, one of the constituents (c), (d) or (e) is added last to the mixture, so that the chain-extension reaction begins only in the dispersion.

As emulsifiers that may be used in the preparation process described above in order to obtain the aqueous dispersion of particles, mention may be made of nonionic or ionic (anionic, cationic or amphoteric) emulsifiers. They are preferably nonionic emulsifiers, which may be chosen from polyalkylene glycol ethers of a fatty alcohol comprising from 8 to 30 carbon atoms and preferably from 10 to 22 carbon atoms; polyoxyalkylenated and especially polyoxyethylenated sorbitan alkyl esters, in which the alkyl radical comprises from 8 to 30 carbon atoms and preferably from 10 to 22 carbon atoms; polyoxyalkylenated and especially polyoxyethylenated alkyl esters, in which the alkyl radical comprises from 8 to 30 carbon atoms and preferably from 10 to 22 carbon atoms; polyethylene glycols; polypropylene glycols; diethylene glycols; and mixtures thereof. The amount of emulsifier(s) is generally from 1% to 30% by weight relative to the total weight of the reaction mixture.

The emulsifier used for obtaining the aqueous particle dispersion is preferably chosen from polyethylene glycol ethers of fatty alcohols and mixtures thereof, and especially polyethylene glycol ethers of alcohols comprising 12 or 13 carbon atoms and from 2 to 100 oxyethylene units and preferably from 3 to 50 oxyethylene units, and mixtures thereof. Mention may be made, for example, of $C_{12}$-$C_{13}$ Pareth-3 and $C_{12}$-$C_{13}$ Pareth-23, and mixtures thereof.

According to a particular embodiment of the invention, the silicone copolymer particle dispersion is obtained from dimethylvinylsiloxypolydimethylsiloxane (or divinyl dimethicone) as compound (i), and from the compound of formula (II) preferably with n=20, as compound (ii), preferably in the presence of a catalyst of platinum type, and the particle dispersion is preferably obtained in the presence of $C_{12}$-$C_{13}$ Pareth-3 and $C_{12}$-$C_{13}$ Pareth-23 as emulsifiers.

Use may especially be made, as a dispersion of silicone copolymer particles, of the product sold under the name HMW 2220 by Dow Corning (CTFA name: divinyl dimethicone/dimethicone copolymer/$C_{12}$-$C_{13}$ Pareth-3/$C_{12}$-$C_{13}$ Pareth-23), which is an aqueous 60% dispersion of divinyl dimethicone/dimethicone copolymer comprising $C_{12}$-$C_{13}$ Pareth-3 and $C_{12}$-$C_{13}$ Pareth-23, the said dispersion comprising approximately 60% by weight of copolymer, 2.8% by weight of $C_{12}$-$C_{13}$ Pareth-23, 2% by weight of $C_{12}$-$C_{13}$ Pareth-3 and 0.31% by weight of preserving agents, the remainder to 100% being water.

The linear block silicone copolymer(s) may be present, for example, in an amount of polymeric active materials ranging from 0.1% to 30% by weight, better still from 0.5% to 20% by weight and even better still from 1% to 15% by weight relative to the total weight of the composition.

According to one embodiment, the hybrid hydrophobic film-forming acrylic polymer(s) and the linear block silicone copolymer(s) are present in a weight ratio (as polymer active materials) of hybrid hydrophobic film-forming acrylic polymer(s) to linear block silicone copolymer(s) ranging from 0.2 to 10, better still from 0.5 to 5 and even better still from 1 to 3.

When the glass transition temperature of the hybrid hydrophobic film-forming acrylic polymer is too high for the desired use, for example a Tg of greater than 40° C., a plasticizer may be combined therewith so as to lower this temperature of the mixture used. The plasticizer may be chosen from the plasticizers usually used in the field of application, and especially from compounds that may be solvents for the polymer.

Preferably, the plasticizer has a molecular mass of less than or equal to 5,000 g/mol, preferably less than or equal to 2,000 g/mol, preferentially less than or equal to 1,000 g/mol and more preferentially less than or equal to 900 g/mol. The plasticizer advantageously has a molecular mass of greater than or equal to 100 g/mol.

Thus, the composition may also comprise at least one plasticizer. In particular, mention may be made, alone or as a mixture, of common plasticizers such as:
- glycols and derivatives thereof, such as diethylene glycol ethyl ether, diethylene glycol methyl ether, diethylene glycol butyl ether or diethylene glycol hexyl ether, ethylene glycol ethyl ether, ethylene glycol butyl ether or ethylene glycol hexyl ether;
- polyethylene glycols, polypropylene glycols, polyethylene glycol-polypropylene glycol copolymers, and mixtures thereof, especially high molecular weight polypropylene glycols, for example having a molecular mass ranging from 500 to 15,000, for instance glycol esters;
- propylene glycol derivatives and in particular propylene glycol phenyl ether, propylene glycol diacetate, dipropylene glycol ethyl ether, tripropylene glycol methyl ether and diethylene glycol methyl ether, dipropylene glycol butyl ether. Such compounds are sold by Dow Chemical under the names Dowanol PPH and Dowanol DPnB;
- acid esters, especially carboxylic acid esters, such as citrates, phthalates, adipates, carbonates, tartrates, phosphates or sebacates;
- esters derived from the reaction of a monocarboxylic acid of formula $R_{11}COOH$ with a diol of formula $HOR_{12}OH$ in which $R_{11}$ and $R_{12}$, which may be identical or different, represent a linear, branched or cyclic, saturated or unsaturated hydrocarbon-based chain preferably containing from 3 to 15 carbon atoms, optionally comprising one or more heteroatoms such as N, O or S, in particular the monoester resulting from the reaction of isobutyric acid and octanediol such as 2,2,4-trimethyl-1,3-pentanediol, such as the product sold under the reference Texanol Ester Alcohol by the company Eastman Chemical;
- oxyethylated derivatives such as oxyethylated oils, especially plant oils such as castor oil;
- mixtures thereof.

More particularly, the plasticizer may be chosen from esters of at least one carboxylic acid containing 1 to 7 carbon atoms and of a polyol comprising at least 4 hydroxyl groups.

The polyol according to the invention may be a cyclized or uncyclized saccharide polyhydroxyaldehyde (aldose) or polyhydroxyketone (ketose). The polyol is preferably a saccharide cyclized in hemiacetal form.

The polyol may be a monosaccharide or a polysaccharide comprising from 1 to 10 saccharides, preferably from 1 to 4 saccharides and more preferably one or two saccharides. The polyol may be chosen from erythritol, xylitol, sorbitol, glucose, sucrose, lactose and maltose.

The polyol according to the invention is preferably a disaccharide. Among the disaccharides, mention may be made of sucrose (also known as α-D-glucopyranosyl-(1-2)-β-D-fructofuranose), lactose (also known as β-D-galactopyranosyl-(1-4)-β-D-glucopyranose) and maltose (also known as α-D-glucopyranosyl-(1-4)-β-D-glucopyranose), and preferably sucrose.

The ester according to the invention may be constituted of a polyol esterified with at least two different monocarboxylic acids, or with at least three different monocarboxylic acids.

The ester according to the invention may be a copolymer of two esters, in particular a copolymer i) of a sucrose substituted with benzoyl groups and ii) of a sucrose substituted with acetyl and/or isobutyryl groups.

The carboxylic acid is preferably a monocarboxylic acid containing from 1 to 7 carbon atoms and preferably from 1 to 5 carbon atoms, chosen, for example, from acetic acid, n-propanoic acid, isopropanoic acid, n-butanoic acid, isobutanoic acid, tert-butanoic acid, n-pentanoic acid and benzoic acid.

The ester may be obtained from at least two different monocarboxylic acids. According to one embodiment, the acid is an unsubstituted linear or branched acid.

The acid is preferably chosen from acetic acid, isobutyric acid and benzoic acid, and mixtures thereof.

According to one preferred embodiment, the ester is sucrose diacetate hexakis(2-methylpropanoate), such as the product sold under the name Sustane SAIB Food Grade Kosher by the company Eastman Chemical.

According to another embodiment, the plasticizer may be chosen from esters of an aliphatic or aromatic polycarboxylic acid and of an aliphatic or aromatic alcohol containing from 1 to 10 carbon atoms.

The aliphatic or aromatic alcohol comprises from 1 to 10 and preferably from 1 to 8 carbon atoms, for example from 1 to 6 carbon atoms. It may be chosen from the alcohols R1OH, such that R1 represents methyl, ethyl, propyl, isopropyl, butyl, hexyl, ethylhexyl, decyl, isodecyl, benzyl, or benzyl substituted with an alkyl comprising 1 to 3 carbon atoms, and mixtures thereof.

The aliphatic or aromatic polycarboxylic acid preferably contains from 3 to 12 carbon atoms, preferably from 3 to 10 carbon atoms and preferably from 3 to 8 carbon atoms, for example 6 or 8 carbon atoms.

The aliphatic or aromatic polycarboxylic acid is advantageously chosen from dicarboxylic acids and tricarboxylic acids.

Among the aliphatic dicarboxylic acids that may be mentioned are those of formula $HOOC-(CH_2)_n-COOH$, in which n is an integer ranging from 1 to 10 and preferably ranging from 2 to 8, for example equal to 2, 4, 6 or 8.

Dicarboxylic acids chosen from succinic acid, adipic acid and sebacic acid are preferred.

Among the aromatic dicarboxylic acids, mention may be made of phthalic acid.

Among the tricarboxylic acids, mention may be made of the triacids that correspond to formula

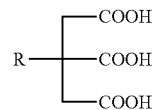

in which R represents a group —H, —OH or —OCOR' in which R' represents an alkyl group containing from 1 to 6 carbon atoms. Preferably, R represents a group —OCOCH$_3$.

The tricarboxylic acid is especially chosen from acetylcitric acid, butyroylcitric acid and citric acid.

Among the tricarboxylic acid esters that may be used are esters derived from citric acid (or citrates) such as tributyl acetyl citrate, triethyl acetyl citrate, triethylhexyl acetyl citrate, trihexyl acetyl citrate, trihexyl butyroyl citrate, triisodecyl citrate, triisopropyl citrate, tributyl citrate and tris (2-ethylhexyl) citrate. As commercial references of plasticizers mentioned above, mention may be made of the Citroflex range sold by Vertellus, especially, Citroflex A4 and Citroflex C2.

Among the adipic acid esters that may be mentioned are dibutyl adipate and bis(2-ethylhexyl) adipate.

Among the sebacic acid esters that may be mentioned are dibutyl sebacate, bis(2-ethylhexyl) sebacate, diethyl sebacate and diisopropyl sebacate.

Among the succinic acid esters that may be mentioned are bis(2-ethylhexyl) succinate and diethyl succinate.

Among the phthalic acid esters that may be mentioned are butyl benzyl phthalate, dibutyl phthalate, diethylhexyl phthalate, diethyl phthalate and dimethyl phthalate.

Advantageously, the plasticizer(s) may be present in the composition in a content such that the mass ratio between the hybrid hydrophobic film-forming acrylic polymer(s) and the plasticizer(s) ranges from 0.5 to 100, preferably from 1 to 50 and preferably from 1 to 10.

Amino Acid or Amino Acid Derivative

The term "amino acid or amino acid derivative" means any compound chosen from synthetic or natural, modified or unmodified amino acids, salts thereof, enantiomers thereof, synthetic or natural oligomers or polymers comprising at least two amino acids, salts thereof and mixtures thereof.

The amino acids and derivatives used in the composition according to the invention comprise at least one amine function and at least one acid function. The acid function(s) may be carboxylic, sulfonic, phosphonic or phosphoric, preferably carboxylic.

The amino acids may especially correspond to the following formula

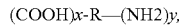

(COOH)$x$-R—(NH2)$y$, in which R is a linear or branched and/or cyclic, saturated or unsaturated hydrocarbon-based chain optionally interrupted with one or more heteroatoms or groups comprising one or more heteroatoms, the said chain and the said rings being optionally substituted, and x and y represent an integer equal to 1 or 2, preferably x=1 and y=1.

Preferably, the amino acids used in the present invention are α-amino acids, i.e. they comprise an amine function and a group R located in the alpha position relative to the acid function. They may be represented by formula (A) below:

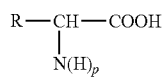

(A)

R—CH—COOH
|
N(H)$_p$ p is equal to 1 or 2, and when p=2, R represents a hydrogen atom, an aliphatic group optionally comprising a heterocyclic portion, or an aromatic group, or when p=1, R may form with the nitrogen atom of —N(H)$_p$ a heterocycle. This heterocycle is preferably a saturated 5-membered ring, optionally substituted with one or more C$_{1-4}$ alkyl or hydroxyl groups.

Preferably, the aliphatic group is a linear or branched C$_1$-C$_4$ alkyl group; a linear or branched C$_1$-C$_4$ hydroxyalkyl group; a linear or branched C$_1$-C$_4$ aminoalkyl group; a linear or branched (C$_1$-C$_4$ alkyl)thio(C$_1$-C$_4$)alkyl group; a linear or branched C$_2$-C$_4$ carboxyalkyl group; a linear or branched ureidoalkyl group, a linear or branched imidazoloalkyl group or a linear or branched indolylalkyl group, the alkyl portions of these last four groups comprising from one to four carbon atoms.

The aromatic group may be a C$_6$ aryl or C$_7$-C$_{10}$ aralkyl group, the aromatic nucleus being optionally substituted with one or more C$_1$-C$_4$ alkyl or hydroxyl groups.

Preferably, when p=2, R represents a hydrogen atom, an aliphatic group chosen from a linear or branched (C$_1$-C$_4$ alkyl)thio(C$_1$-C$_4$)alkyl group, a linear or branched imidazoloalkyl group, a linear or branched indolylalkyl group, the alkyl portions of these last two groups comprising from one to four carbon atoms or a C$_7$-C$_{10}$ aralkyl group, the aromatic nucleus being optionally substituted with one or more C$_1$-C$_4$ alkyl or hydroxyl groups, especially a phenyl or hydroxyphenyl group.

As amino acids that may be used in the present invention, mention may be made especially of alanine, glycine, isoleucine, leucine, methionine, proline, tyrosine, valine, cysteine, phenylalanine, preferably in their L form, tryptophan, in particular D-tryptophan, or mixtures thereof, and also salts thereof.

The amino acid derivatives may also be chosen from:
  modified amino acids, especially:
    N-acylamino acids, the acyl group comprising from 10 to 30 carbon atoms and preferably from 12 to 22 carbon atoms, for instance amino acids that are preferably not polycarboxylic and/or not water-soluble (solubility of less than 1% at pH 7 and at 25° C.), substituted with a lauroyl, myristoyl, palmitoyl, stearoyl, behenyl, olivoyl or cocoyl group, for instance lauroyl-L-lysine;
    amino acids substituted with a carboxyalkyl group, especially a carboxymethyl group, for instance carboxymethylcysteine,
  synthetic or natural oligomers or polymers comprising at least two amino acids. They may be homopolymers or copolymers of natural or modified amino acids.
    Homopolymers that may be mentioned include polylysines, poly-β-alanines and polyaspartic acids.
    Amino acid oligomers or polymers that may also be mentioned include proteins or protein hydrolysates, such as soybean (glycine) proteins, for instance the glycine soya protein dispersion sold under the reference Eleseryl HGP LS 9874 by the company Laboratoires Sérobiologigues, or silk proteins such as the silk protein powder sold by the company Croda.

The amino acids or derivatives thereof may be present in the composition in their native form or supplied by a compound bearing an amino acid or a derivative, for example a particle (filler, pigment) surface-treated with an amino acid or an amino acid derivative.

The amino acids or derivatives thereof may be present in the composition in a content ranging from 0.001% to 20% by weight, especially from 0.01% to 10% by weight and preferentially from 0.05% to 5% by weight relative to the total weight of the composition.

Thickener

The composition that is useful in the device or the process of the invention may comprise a thickener. This thickener may be chosen from mineral or organic, polymeric or non-polymeric thickeners, and mixtures thereof.

This or these thickener(s) may be present in a total content ranging from 0.01% to 10% by weight, especially from 0.1% to 5% by weight and preferentially from 0.2% to 3% by weight, relative to the total weight of the composition.

According to one particular embodiment of the invention, the composition comprises at least one mineral thickener.

Preferably, the additional thickener(s) are chosen from fumed silica and clays, or mixtures thereof.

The fumed silicas may be obtained by high-temperature pyrolysis of a volatile silicon compound in an oxhydric flame, producing a finely divided silica. This process makes it possible especially to obtain hydrophilic silicas which bear a large number of silanol groups at their surface. Such hydrophilic silicas are sold, for example, under the names Aerosil 130®, Aerosil 200®, Aerosil 255®, Aerosil 300® and Aerosil 380® by Degussa and Cab-O-Sil HS-5®, Cab-O-Sil EH-5®, Cab-O-Sil LM-130®, Cab-O-Sil MS-55® and Cab-O-Sil M-5® by Cabot.

It is possible to chemically modify the surface of the said silica, via a chemical reaction generating a reduction in the number of silanol groups. It is possible in particular to replace silanol groups with hydrophobic groups: a hydrophobic silica is then obtained.

The hydrophobic groups may be:

trimethylsiloxyl groups, which are obtained especially by treating fumed silica in the presence of hexamethyldisilazane. Silicas thus treated are known as "Silica silylate" according to the CTFA (6th edition, 1995). They are sold, for example, under the references Aerosil R812® by the company Degussa and Cab-O-Sil TS-530® by the company Cabot.

dimethylsilyloxyl or polydimethylsiloxane groups, which are obtained in particular by treating fumed silica in the presence of polydimethylsiloxane or dimethyldichlorosilane. Silicas thus treated are known as Silica Dimethyl Silylate according to the CTFA (6th edition, 1995). They are sold, for example, under the references Aerosil R972® and Aerosil R974® by the company Degussa, and Cab-O-Sil TS-610® and Cab-O-Sil TS-720® by the company Cabot.

The fumed silica preferably has a particle size that may be nanometric to micrometric, for example ranging from about 5 to 200 nm.

Clays are products that are well known, and which are described, for example, in the publication *Minéralogie des argiles* [Mineralogy of Clays], S. Caillère, S. Hénin, M. Rautureau, 2nd Edition 1982, Masson.

Clays are silicates containing a cation that may be chosen from calcium, magnesium, aluminium, sodium, potassium and lithium cations, and mixtures thereof.

Examples of such products that may be mentioned include clays of the smectite family such as montmorillonites, hectorites, bentonites, beidellites and saponites, and also of the vermiculite, stevensite and chlorite families.

These clays may be of natural or synthetic origin. Clays that are cosmetically compatible and acceptable with keratin materials are preferably used.

As clays that may be used according to the invention, mention may be made of synthetic hectorites (also known as laponites), for instance the products sold by the company Laporte under the name Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the product sold by the Vanderbilt Company under the name Veegum Ultra, or calcium silicates and especially the product in synthetic form sold by the company under the name Micro-cel C.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylaryl sulfonates and amine oxides, and mixtures thereof.

Mention may be made, as organophilic clays, of quaternium-18 bentonites, such as those sold under the names Bentone 3, Bentone 38 and Bentone 38V by Rheox, Tixogel VP by United Catalyst and Claytone 34, Claytone 40 and Claytone XL by Southern Clay; stearalkonium bentonites, such as those sold under the names Bentone 27 by Rheox, Tixogel LG by United Catalyst and Claytone AF and Claytone APA by Southern Clay; and quaternium-18/benzalkonium bentonites, such as those sold under the names Claytone HT and Claytone PS by Southern Clay.

The thickener may also be chosen from organic thickeners. Examples that may be mentioned include the following non-polymeric products:

$C_{10}$-$C_{30}$ fatty amides such as lauric acid diethanolamide. Mention may also be made of the following organic thickening polymers:

the polyglyceryl (meth)acrylate polymers sold under the names Hispagel and Lubragel by the companies Hispano Quimica or Guardian, polyvinylpyrrolidone, polyvinyl alcohol, crosslinked acrylamide polymers and copolymers, such as those sold under the names PAS 5161 or Bozepol C by the company Hoechst, Sepigel 305 by the company SEPPIC by the company Allied Colloid, or the crosslinked methacryloyloxyethyltrimethylammonium chloride homopolymers sold under the name Salcare SC95 by the company Allied Colloid, (meth)acrylamido($C_1$-$C_4$)alkylsulfonic acid homopolymers, which are preferably crosslinked, in particular crosslinked poly-2-acrylamido-2-methylpropanesulfonic acid homopolymers partially neutralized with ammonia, crosslinked acrylic acid homopolymers, acrylate/$C_{10}$-$C_{30}$ alkylacrylate copolymers, associative polyurethanes, celluloses, in particular hydroxyalkylcelluloses such as hydroxyethylcelluloses, and mixtures thereof.

The thickening polymers are preferably polymers having, as a solution or dispersion containing 1% by weight of active material in water or in ethanol, at 25° C., a viscosity greater than 0.2 poise at a shear rate of 1 $s^{-1}$. The viscosity is measured with a Haake RS600 viscometer from Thermo Electron. This viscometer is a controlled-stress viscometer with cone-plate geometry (for example having a diameter of 60 mm).

The composition according to the invention comprises water, which may preferably be present in a content ranging from 20% to 98% by weight relative to the weight of the composition.

According to a particular embodiment, the composition of the invention contains an odorous compound or a mixture of odorous compounds, such as a perfume. Odorous compounds and perfumes that may be mentioned include those described in the article *Perfumes* by William L. Schreiber, pp. 171-201 volume 18 of the 4th edition of Kirk Othmer's *Encyclopaedia of Chemical Technology*, 1996.

The compositions may also contain at least one agent usually used in cosmetics, chosen, for example, from reducing agents, fatty substances, organic solvents or oils, softeners, antifoams, moisturizers, UV-screening agents, peptizers, solubilizers, anionic, cationic, nonionic or amphoteric surfactants, proteins, vitamins, propellants, oxyethylenated or non-oxyethylenated waxes, paraffins, $C_{10}$-$C_{30}$ fatty acids such as stearic acid or lauric acid, direct dyes, pigments and fillers, and mixtures thereof.

The above additives are generally present in an amount for each of them of between 0.01% and 20% by weight relative to the weight of the composition.

Pigments

The composition may comprise one or more pigments.

Such a composition makes it possible to obtain coloured and long-lasting coatings, without degradation of the keratin fibres, and with all the advantages described previously.

The term "pigments" means white or coloured particles of any shape, which are insoluble in the composition in which they are present.

The pigments that may be used are chosen especially from organic and/or mineral pigments known in the art, in particular those described in Kirk-Othmer's *Encyclopedia of Chemical Technology* and in Ullmann's *Encyclopedia of Industrial Chemistry*.

They may be natural, of natural origin, or non-natural.

These pigments may be provided in pigment powder or paste form. They can be coated or uncoated.

The pigments may be chosen, for example, from mineral pigments, organic pigments, lakes, special-effect pigments, such as nacres or glitter flakes, and mixtures thereof.

The pigment may be a mineral pigment. The term "mineral pigment" means any pigment that satisfies the definition in Ullmann's encyclopaedia in the chapter on inorganic pigments. Among the mineral pigments that are useful in the present invention, mention may be made of ochres such as red ochre (clay (in particular kaolinite) and iron hydroxide (for example haematite)), brown ochre (clay (in particular kaolinite) and limonite), yellow ochre (clay (in particular kaolinite) and goethite); titanium dioxide, optionally surface-treated; zirconium oxide or cerium oxide; zinc oxide, iron oxide (black, yellow or red) or chromium oxide; manganese violet, ultramarine blue, chromium hydrate and ferric blue; metal powders such as aluminium powder or copper powder.

Mention may also be made of alkaline-earth metal carbonates (such as calcium carbonate or magnesium carbonate), silicon dioxide, quartz and any other compound used as inert filler in cosmetic compositions, provided that these compounds contribute colour or whiteness to the composition under the conditions under which they are employed.

The pigment may be an organic pigment. The term "organic pigment" means any pigment that satisfies the definition in Ullmann's encyclopaedia in the chapter on organic pigments.

The organic pigment may especially be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

Use may also be made of any mineral or organic compound that is insoluble in the composition and standard in cosmetics, provided that these compounds afford the composition colour or whiteness under the conditions in which they are used, for example guanine, which, according to the refractive index of the composition, is a pigment.

In particular, the white or coloured organic pigments may be selected from carmine lake, carbon black, aniline black, azo yellow, quinacridone, phthalocyanine blue, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

Examples that may also be mentioned include pigmentary pastes of organic pigments, such as the products sold by the company Hoechst under the names:

Cosmenyl Yellow IOG: Pigment Yellow 3 (CI 11710);
Cosmenyl Yellow G: Pigment Yellow 1 (CI 11680);
Cosmenyl Orange GR: Pigment Orange 43 (CI 71105);
Cosmenyl Red R: Pigment Red 4 (CI 12085);
Cosmenyl Carmine FB: Pigment Red 5 (CI 12490);
Cosmenyl Violet RL: Pigment Violet 23 (CI 51319);
Cosmenyl Blue A2R: Pigment Blue 15.1 (CI 74160);
Cosmenyl Green GG: Pigment Green 7 (CI 74260);
Cosmenyl Black R: Pigment Black 7 (CI 77266).

The pigments in accordance with the invention may also be in the form of composite pigments, as described in patent EP 1 184 426. These composite pigments may be especially composed of particles comprising a mineral core, at least one binder for binding the organic pigments to the core, and at least one organic pigment at least partially covering the core.

The organic pigment may also be a lake. The term "lake" means dyes adsorbed onto insoluble particles, the assembly thus obtained remaining insoluble during use.

The mineral substrates onto which the dyes are adsorbed are, for example, alumina, silica, calcium sodium borosilicate, calcium aluminium borosilicate and aluminium.

Among the dyes, mention may be made of carminic acid. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 O (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a coloured appearance (characterized by a certain shade, a certain vivacity and a certain level of luminance) that is non-uniform and that changes as a function of the conditions of observation (light, temperature, angles of observation, etc.). They thus contrast with coloured pigments that afford a standard uniform opaque, semi-transparent or transparent shade.

Several types of pigment with special effects exist: those with a low refractive index, such as fluorescent, photochromic or thermochromic pigments, and those with a higher refractive index, such as nacres, interference pigments or glitter flakes.

Examples of pigments with special effects that may be mentioned include nacreous pigments such as mica coated with titanium or with bismuth oxychloride, coloured nacreous pigments such as titanium mica with iron oxides, mica covered with iron oxide, titanium mica especially with ferric blue or with chromium oxide, titanium mica with an organic pigment of the abovementioned type, and also nacreous pigments based on bismuth oxychloride. Nacreous pigments that may be mentioned include the nacres Cellini sold by Engelhard (mica-$TiO_2$-lake), Prestige sold by Eckart (mica-$TiO_2$), Prestige Bronze sold by Eckart (mica-$Fe_2O_3$) and Colorona sold by Merck (mica-$TiO_2$—$Fe_2O_3$).

Mention may also be made of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale 0005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles having a glass substrate coated with titanium oxide are especially sold under the name Metashine MC108ORY by the company Toyal.

Finally, examples of nacres that may also be mentioned include polyethylene terephthalate flakes, especially those sold by the company Meadowbrook Inventions under the name Silver 1P 0.004×0.004 (silver flakes).

Multilayer pigments based on synthetic substrates such as alumina, silica, sodium calcium borosilicate or calcium aluminium borosilicate, and aluminium, may also be envisaged.

The special-effect pigments may also be chosen from reflective particles, i.e. especially from particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular in spherical form.

The reflective particles, whatever their form, may or may not have a multilayer structure and, in the case of a multilayer structure, may have, for example, at least one layer of uniform thickness, in particular of a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be made of one or more organic and/or mineral materials.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Use may also be made of particles comprising a metal substrate, such as silver, aluminium, iron, chromium, nickel, molybdenum, gold, copper, zinc, tin, magnesium, steel, bronze or titanium, the said substrate being coated with at least one layer of at least one metal oxide, such as titanium oxide, aluminium oxide, iron oxide, cerium oxide, chromium oxide, silicon oxides and mixtures thereof.

Examples that may be mentioned include aluminium powder, bronze powder or copper powder coated with $SiO_2$ sold under the name Visionaire by the company Eckart.

Mention may also be made of pigments with an interference effect not bound to a substrate, for instance liquid crystals (Helicones HC from Wacker), holographic interference flakes (Geometric Pigments or Spectra f/x from Spectratek). The pigments with special effects also comprise fluorescent pigments, whether they are substances that are fluorescent in daylight or that produce ultraviolet fluorescence, phosphorescent pigments, photochromic pigments, thermochromic pigments and quantum dots, for example sold by the company Quantum Dots Corporation.

Quantum dots are luminescent semiconductor nanoparticles capable of emitting, under light excitation, radiation exhibiting a wavelength of between 400 nm and 700 nm. These nanoparticles are known from the literature. In particular, they may be manufactured according to the processes described, for example, in U.S. Pat. No. 6,225,198 or 5,990,479, in the publications cited therein and also in the following publications: Dabboussi B. O. et al., "(CdSe)ZnS core-shell quantum dots: synthesis and characterization of a size series of highly luminescent nanocrystallites", Journal of Physical Chemistry B, vol. 101, 1997, pp. 9463-9475, and Peng, Xiaogang et al., "Epitaxial growth of highly luminescent CdSe/CdS core/shell nanocrystals with photostability and electronic accessibility", Journal of the American Chemical Society, vol. 119, No. 30, pp. 7019-7029.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 µm, preferably between 20 nm and 80 µm and more preferentially between 30 nm and 50 µm.

The pigments may be dispersed in the product by means of a dispersant.

The dispersant serves to protect the dispersed particles against agglomeration or flocculation. This dispersant may be a surfactant, an oligomer, a polymer or a mixture of several thereof, bearing one or more functionalities with strong affinity for the surface of the particles to be dispersed. In particular, they can physically or chemically attach to the surface of the pigments. These dispersants also contain at least one functional group that is compatible with or soluble in the continuous medium. In particular, 12-hydroxystearic acid esters and $C_8$ to $C_{20}$ fatty acid esters of polyols such as glycerol or diglycerol are used, such as poly(12-hydroxystearic acid) stearate with a molecular weight of about 750 g/mol, such as the product sold under the name Solsperse 21,000 by the company Avecia, polyglyceryl-2 dipolyhydroxystearate (CTFA name) sold under the reference Dehymyls PGPH by the company Henkel, or poly-hydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17,000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in *Cosmetics and Toiletries*, February 1990, vol. 105, pp. 53-64, before being dispersed in the composition that is useful in the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polyethylene; (meth)acrylic polymers, for example polymethyl methacrylates; polymers and copolymers containing acrylate units; alkanolamines; silicone compounds, for example silicones, polydimethylsiloxanes; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigments.

Preferably, the surface treatments of the pigments are chosen from the following treatments:

- a PEG-silicone treatment, for instance the AQ surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- an aluminium dimyristate treatment, for instance the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a disodium stearoyl glutamate treatment, for instance the NAI surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;

a polymethylhydrogensiloxane/perfluoroalkyl phosphate treatment, for instance the FS01 surface treatment sold by Daito;

an acrylate/dimethicone copolymer treatment, for instance the ASC surface treatment sold by Daito;

an isopropyl titanium triisostearate treatment, for instance the ITT surface treatment sold by Daito;

an acrylate copolymer treatment, for instance the APD surface treatment sold by Daito;

a perfluoroalkyl phosphate/isopropyl titanium triisostearate treatment, for instance the PF+ITT surface treatment sold by Daito.

Preferably, the pigment is chosen from mineral or mixed mineral-organic pigments.

The amount of pigment(s) may range from 0.01% to 30%, more particularly from 0.05% to 20% and preferably from 0.1% to 15% by weight relative to the total weight of the composition.

According to another embodiment, the composition according to the invention is non-colouring.

The term "non-colouring composition" means a composition which does not give keratin fibres a new colour by means of one or more dyestuffs. The composition according to the invention therefore does not contain such materials and in particular does not contain any pigments or oxidation dyes, and, if it does contain soluble direct dyes, they are in a concentration (generally less than 0.005%) such that there is coloration of the composition without any colouring effect on the keratin fibres.

Needless to say, a person skilled in the art will take care to select this or these optional additive(s) such that the advantageous properties intrinsically associated with the formation of the coating in accordance with the invention are not, or are not substantially, adversely affected.

The composition according to the invention may especially be in the form of a suspension, a dispersion, a gel, an emulsion, especially an oil-in-water (O/W) or water-in-oil (W/O) emulsion, or a multiple emulsion (W/O/W or polyol/O/W or O/W/O), in the form of a cream, a mousse, a stick, a dispersion of vesicles, especially of ionic or nonionic lipids, a two-phase or multi-phase lotion, a spray or a paste. The composition may also be in the form of a lacquer.

A person skilled in the art may select the appropriate galenical form, and also the method for preparing it, on the basis of his general knowledge, taking into account firstly the nature of the constituents used, especially their solubility in the support, and secondly the intended application of the composition.

The composition described above may be used on wet or dry keratin fibres, and also on any type of fair or dark, natural or dyed, permanent-waved, bleached or relaxed fibres. It may be applied by any suitable means, for example with a brush, by finger or with an applicator bottle.

In particular, the composition may be applied by means of a container comprising a removable applicator end piece comprising a permeable material through which the composition can pass, the composition being applied by placing the applicator in contact with the fibres; such a device is described especially in U.S. Pat. No. 5,961,665 (Fishmann).

According to one embodiment, the composition according to the invention is applied by means of a device comprising:

i) an application means that is capable of retaining an amount of the said composition in a container, ii) a holding member that is capable of engaging with the application means in order, when the device is moved longitudinally (relative to a lock of hair), to hold the said lock in contact with the application means so as to allow it to be coated with the said composition, characterized in that:

the said application means comprises an applicator end piece mounted on the container and comprising an outlet orifice equipped with an opening/closing element which, in a first position, closes off the said outlet orifice and which, in a second position, at least partly releases the said outlet orifice, the movement from the first position to the second position taking place in response to a force exerted on the opening/closing element by the lock being inserted between the holding member and this opening/closing element.

Such a device is especially described in patent FR 2976461.

According to one particular embodiment of the process of the invention, the fibres are washed before application of the composition described above.

After application of the composition, the fibres may be left to dry or dried, for example at a temperature above or equal to 30° C. The drying, if it is performed, may be performed immediately after the application or after a leave-on time that may range from 1 minute to 30 minutes.

Preferably, if the fibres are dried, then in addition to supplying heat, they are dried with a flow of air. This flow of air during drying makes it possible to improve the individualization of the coating.

During drying, a mechanical action may be exerted on the locks, such as combing, brushing or running the fingers through the hair. This operation may similarly be performed once the fibres have been dried, naturally or otherwise.

The drying step of the process of the invention may be performed with a hood, a hairdryer, a straightening iron, a Climazon, etc.

When the drying step is performed with a hood or a hairdryer, the drying temperature is between 40 and 110° and preferably between 50 and 90°.

The application of the composition may be followed by a step of shaping the fibres by finger or by using a device such as a comb, a brush, straightening tongs or a crimping iron. After such a treatment of the fibres, the shape given is shampoo-fast.

When the drying step is performed with a straightening or crimping iron, the drying temperature is between 110 and 220° C. and preferably between 140 and 200° C.

The examples that follow serve to illustrate the invention without, however, being limiting in nature. Unless otherwise mentioned, the amounts indicated are weight percentages.

EXAMPLES

| Composition A | |
|---|---|
| Styrene/acrylate copolymer in aqueous dispersion, sold by BASF under the name Joncryl 77 | 21.2 g, i.e. 10 g of AM |
| Divinyl dimethicone/dimethicone copolymer as an aqueous emulsion, sold by Dow Corning under the reference HMW 2220 Nonionic Emulsion | 8.3 g, i.e. 5 g of AM |
| Glycine sold by Ajinomoto | 2 g |
| Black 2 as an aqueous dispersion, from Daito Kasei Kogyo under the name WD-CB2 | 10 g, i.e. 2.5 g of AM |
| Water | qs 100 g |

0.6 g of composition A is applied to a 1 g lock of grey hair. After a few seconds, the lock of hair is dried, the hair is dyed, and the colour is uniform and persistent on shampooing a few times. The hair is soft and the hairs may be individualized with the fingers or by using a comb and/or a brush.

| Composition B | |
|---|---|
| Styrene/acrylate copolymer in aqueous dispersion, sold by BASF under the name Joncryl 77 | 21.2 g, i.e. 10 g of AM |
| Divinyl dimethicone/dimethicone copolymer as an aqueous emulsion, sold by Dow Corning under the reference HMW 2220 Nonionic Emulsion | 8.3 g, i.e. 5 g of AM |
| Nacre of mica coated with brown iron oxide, sold by Eckart under the name Prestige Soft Bronze | 6 g |
| L-Alanine (Ajinomoto) | 1.5 g |
| Water | qs 100 g |

0.7 g of composition B is applied to a 1 g lock of hair with a tone depth of 4.
The lock dries after a few seconds, and is shaped into a curl using a straightening iron. When the treated lock is placed in a beaker containing water, the shape of the curl is retained when the hair is wet and after drying in the open air.

| Composition C | |
|---|---|
| Styrene/acrylate copolymer in aqueous dispersion, sold by BASF under the name Joncryl 77 | 20 g of AM, i.e. 9.4 g of AM |
| Divinyl dimethicone/dimethicone copolymer as an aqueous emulsion, sold by Dow Corning under the reference HMW 2220 Nonionic Emulsion | 7.9 g, i.e. 4.75 g of AM |
| N-Lauroyl L-lysine (Mihope LL from Ajinomoto) | 2.5 g |
| Black 2 as an aqueous dispersion, from Daito Kasei Kogyo under the name WD-CB2 | 9 g, i.e. 2.25 g of AM |
| Water | qs 100 g |

0.6 g of composition C is applied to a 1 g lock of grey hair. After a few seconds, the lock of hair is dried, the hair is dyed, and the colour is uniform and persistent on shampooing a few times. The hair is soft and the hairs may be individualized with the fingers or by using a comb and/or a brush.

| Composition D | |
|---|---|
| Styrene/acrylate copolymer in aqueous dispersion, sold by BASF under the name Joncryl 77 | 20 g, i.e. 9.4 g of AM |
| Divinyl dimethicone/dimethicone copolymer as an aqueous emulsion, sold by Dow Corning under the reference HMW 2220 Nonionic Emulsion | 7.9 g, i.e. 4.75 g of AM |
| Silk protein powder (Crosilk Powder from Croda) | 2 g |
| Black 2 as an aqueous dispersion, from Daito Kasei Kogyo under the name WD-CB2 | 10 g, i.e. 2.5 g of AM |
| Water | qs 100 g |

0.6 g of composition D is applied to a 1 g lock of grey hair. After a few seconds, the lock of hair is dried, the hair is dyed, and the colour is uniform and persistent on shampooing a few times. The hairs may be individualized with the fingers or by using a comb and/or a brush.

| Composition E | |
|---|---|
| Styrene/acrylate copolymer in aqueous dispersion, sold by BASF under the name Joncryl 77 | 21.2 g, i.e. 10 g of AM |
| Divinyl dimethicone/dimethicone copolymer as an aqueous emulsion, sold by Dow Corning under the reference HMW 2220 Nonionic Emulsion | 8.3 g, i.e. 5 g of AM |
| Glycine soya protein dispersion containing 6% active material (Eleseryl HGP LS 9874 from Laboratoires Sérobiologiques) | 3 g |

| Composition E | |
|---|---|
| Nacre of mica coated with brown iron oxide, sold by Eckart under the name Prestige Soft Bronze | 5 g |
| Water | qs 100 g |

0.6 g of composition E is applied to a 1 g lock of grey hair. After a few seconds, the lock of hair is dried, the hair is dyed, and the colour is uniform and persistent on shampooing a few times. The hairs may be individualized with the fingers or by using a comb and/or a brush.

The invention claimed is:

1. A process for dyeing a head of hair, comprising:
applying to the head of hair a hair dyeing composition comprising:
an aqueous dispersion of hybrid hydrophobic film-forming acrylic polymer particles, present in an amount ranging from 1% to 15% by weight, relative to the total weight of the composition;
at least one linear block silicone copolymer present in an amount ranging from 1% to 15% by weight, relative to the total weight of the composition;
at least one amino acid present in an amount ranging from 0.05% to 5% by weight relative to the total weight of the composition, wherein the at least one amino acid is chosen from alanine, glycine, isoleucine, leucine, proline, tyrosine, valine, phenylalanine, tryptophan, mixtures thereof, or salts thereof; and
at least one pigment, present in an effective amount to dye the head of hair;
wherein the hybrid hydrophobic film-forming acrylic polymer particles are prepared from:
(i) at least one compound (i) chosen from: monomers bearing at least one (meth)acrylic acid group, esters of monomers bearing at least one (meth)acrylic acid group, or amides of monomers bearing at least one (meth)acrylic acid group; and
(ii) at least one compound (ii) chosen from styrene compounds; and
wherein the hybrid hydrophobic film-forming acrylic polymer particles and the at least one linear block silicone copolymer are present in a weight ratio ranging from 1 to 3.

2. The process according to claim 1, wherein the at least one linear block silicone copolymer is in the form of an aqueous dispersion of particles in an aqueous medium.

3. The process according to claim 1, wherein the at least one linear block silicone copolymer is obtained by a chain-extension reaction, in the presence of a catalyst, using at least:
a polysiloxane (i) bearing at least one reactive group; and
an organosilicon compound (ii) which reacts with the polysiloxane (i) via a chain-extension reaction.

4. The process according to claim 3, wherein the polysiloxane (i) is chosen from the following polymers of formula (I):

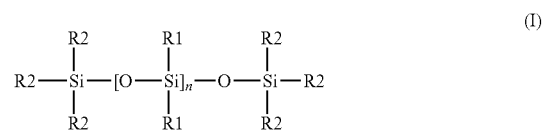

wherein:
R$_1$ and R$_2$ each independently represent a hydrocarbon-based group containing from 1 to 20 carbon atoms, an aryl group, or a reactive group; and
n is an integer greater than 1,
wherein each polymer contains an average of between one and two reactive groups.

5. The process according to claim 4, wherein the reactive groups in the polysiloxane are independently chosen from hydrogen, aliphatically unsaturated groups, a hydroxyl group, alkoxy groups, alkoxyalkoxy groups, an acetoxy group, amine groups, and mixtures thereof.

6. The process according to claim 4, wherein R$_1$ represents a methyl group and R$_2$ at the at least one end of a chain represents a vinyl group.

7. The process according to claim 3, wherein the organosilicon compound (ii) is chosen from the polysiloxanes of formula (I) and compounds acting as chain extenders.

8. The process according to the claim 7, wherein the organosilicon compound (ii) is a liquid organohydrogenpolysiloxane chosen from those of formula (II) below:

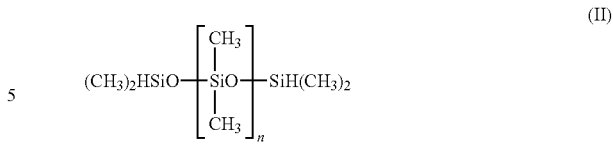
(II)

wherein n is an integer greater than 1.

9. The process according to claim 2, wherein the aqueous dispersion of linear block silicone copolymer particles comprises an aqueous dispersion of divinyl dimethicone/dimethicone copolymer particles.

10. The process according to claim 1, wherein the at least one amino acid is chosen from L-alanine, L-glycine, L-isoleucine, L-leucine, L-proline, L-tyrosine, L-valine, L-phenylalanine, D-tryptophan, mixtures thereof, or salts thereof.

11. The process according to claim 1, wherein the at least one pigment is present in an amount ranging from 0.1 to 30% by weight relative to the total weight of the composition.

\* \* \* \* \*